United States Patent
Dudasik et al.

(10) Patent No.: US 8,323,292 B2
(45) Date of Patent: Dec. 4, 2012

(54) ADJUSTABLE PIN DRILL GUIDE AND METHODS THEREFOR

(75) Inventors: Michael W. Dudasik, Nutley, NJ (US); Zoya Royt, Fresh Meadows, NY (US); Jean-Jacques Abitol, San Diego, CA (US); Joseph P. Errico, Green Brook, NJ (US)

(73) Assignee: SpineCore, Inc., Allendale, NJ (US)

( * ) Notice: Subject to any disclaimer, the term of this patent is extended or adjusted under 35 U.S.C. 154(b) by 855 days.

(21) Appl. No.: 12/316,660

(22) Filed: Dec. 15, 2008

(65) Prior Publication Data

US 2010/0152745 A1  Jun. 17, 2010

(51) Int. Cl.
- *A61B 17/58* (2006.01)
- *A61B 17/60* (2006.01)
- *A61F 2/00* (2006.01)

(52) U.S. Cl. .............. 606/96; 606/87; 606/105

(58) Field of Classification Search .......... 606/90, 606/96–99, 104, 105
See application file for complete search history.

(56) References Cited

U.S. PATENT DOCUMENTS

| | | | |
|---|---|---|---|
| 2,181,746 A | 11/1939 | Siebrandt |
| 2,540,574 A | 2/1951 | Feucht |
| 2,607,339 A | 8/1952 | Price |
| 3,945,377 A | 3/1976 | Kronner |
| 4,257,411 A | 3/1981 | Cho |
| 4,444,180 A | 4/1984 | Schneider et al. |
| 4,672,975 A | 6/1987 | Sirota |
| 4,714,469 A | 12/1987 | Kenna |
| 4,907,577 A | 3/1990 | Wu |
| 4,920,959 A | 5/1990 | Witzel et al. |
| 5,071,437 A | 12/1991 | Steffee |
| 5,258,031 A | 11/1993 | Salib et al. |
| 5,423,826 A | 6/1995 | Coates et al. |
| 5,425,773 A | 6/1995 | Boyd et al. |
| 5,534,029 A | 7/1996 | Shima |
| 5,562,738 A | 10/1996 | Boyd et al. |
| 5,571,109 A | 11/1996 | Bertagnoli |

(Continued)

FOREIGN PATENT DOCUMENTS

EP  0 421 485  4/1991

(Continued)

OTHER PUBLICATIONS

European Search Report, EP09179132, Dated Apr. 8, 2010.

*Primary Examiner* — Andrew Yang
(74) *Attorney, Agent, or Firm* — Lerner, David, Littenberg, Krumholz & Mentlik, LLP

(57) ABSTRACT

An adjustable pin drill guide and method for using an adjustable pin drill guide to prepare a vertebral body space to receive an implant are disclosed. The method includes providing an adjustable pin drill guide, producing a gap by removing tissue between a first vertebral body and a second vertebral body, inserting into the gap first and second extensions of the guide in a first position, moving the first extension and the second extension to a second position, drilling a first hole in the first vertebral body through a first opening in the guide, drilling a second hole in the second vertebral body through a second opening in the guide, placing a first pin into the first hole, and placing a second pin into the second hole. The first and second extensions are preferably in parallel planes when in the first and second positions.

9 Claims, 20 Drawing Sheets

U.S. PATENT DOCUMENTS

| | | |
|---|---|---|
| 5,669,915 A | 9/1997 | Caspar et al. |
| 5,681,320 A | 10/1997 | McGuire |
| 5,782,832 A | 7/1998 | Larsen et al. |
| 5,810,828 A | 9/1998 | Lightman et al. |
| 5,824,094 A | 10/1998 | Serhan et al. |
| 5,851,207 A | 12/1998 | Cesarone |
| 5,888,227 A | 3/1999 | Cottle |
| 5,895,389 A | 4/1999 | Schenk et al. |
| 5,895,428 A | 4/1999 | Berry |
| 5,899,941 A | 5/1999 | Nishijima et al. |
| 6,056,749 A | 5/2000 | Kuslich |
| 6,066,142 A | 5/2000 | Serbousek et al. |
| 6,096,080 A | 8/2000 | Nicholson et al. |
| 6,139,579 A | 10/2000 | Steffee et al. |
| 6,146,421 A | 11/2000 | Gordon et al. |
| 6,162,252 A | 12/2000 | Kuras et al. |
| 6,228,118 B1 | 5/2001 | Gordon |
| 6,287,313 B1 | 9/2001 | Sasso |
| 6,332,887 B1 | 12/2001 | Knox |
| 6,342,057 B1 | 1/2002 | Brace et al. |
| 6,348,071 B1 | 2/2002 | Steffee et al. |
| 6,379,364 B1 | 4/2002 | Brace et al. |
| 6,478,800 B1 | 11/2002 | Fraser et al. |
| 6,517,544 B1 | 2/2003 | Michelson |
| 6,517,580 B1 | 2/2003 | Ramadan et al. |
| 6,520,993 B2 | 2/2003 | James et al. |
| 6,537,279 B1 | 3/2003 | Michelson |
| 6,540,785 B1 | 4/2003 | Gill et al. |
| 6,592,624 B1 | 7/2003 | Fraser et al. |
| 6,616,695 B1 | 9/2003 | Crozet et al. |
| 6,660,038 B2 | 12/2003 | Boyer, II et al. |
| 6,669,698 B1 | 12/2003 | Tromanhauser et al. |
| 6,669,732 B2 | 12/2003 | Serhan et al. |
| 7,749,231 B2 * | 7/2010 | Bonvallet et al. ............... 606/99 |
| 2001/0016773 A1 | 8/2001 | Serhan et al. |
| 2002/0022888 A1 | 2/2002 | Serhan et al. |
| 2002/0099443 A1 | 7/2002 | Messerli et al. |
| 2002/0133172 A1 | 9/2002 | Lambrecht et al. |
| 2003/0032962 A1 | 2/2003 | McGahan et al. |
| 2003/0040802 A1 | 2/2003 | Errico et al. |
| 2003/0045940 A1 | 3/2003 | Eberlein et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0083667 A1 | 5/2003 | Ralph et al. |
| 2003/0100908 A1 | 5/2003 | Grumberg et al. |
| 2003/0105527 A1 | 6/2003 | Bresina |
| 2003/0109928 A1 | 6/2003 | Pasquet et al. |
| 2003/0167091 A1 | 9/2003 | Scharf |
| 2003/0176925 A1 | 9/2003 | Paponneau |
| 2003/0181981 A1 | 9/2003 | Lemaire |
| 2003/0191533 A1 | 10/2003 | Dixon et al. |
| 2003/0191534 A1 | 10/2003 | Viart et al. |
| 2003/0204261 A1 | 10/2003 | Eisermann et al. |
| 2003/0208272 A1 | 11/2003 | Crozet et al. |
| 2003/0233145 A1 | 12/2003 | Landry et al. |
| 2003/0233146 A1 | 12/2003 | Grinberg et al. |
| 2003/0236571 A1 | 12/2003 | Ralph et al. |
| 2004/0002758 A1 | 1/2004 | Landry et al. |
| 2004/0010316 A1 | 1/2004 | William et al. |
| 2004/0102787 A1 | 5/2004 | Bimman |
| 2004/0186482 A1 | 9/2004 | Kolb et al. |
| 2004/0204710 A1 | 10/2004 | Patel et al. |
| 2004/0204716 A1 | 10/2004 | Fanger et al. |
| 2004/0204717 A1 | 10/2004 | Fanger et al. |
| 2004/0210232 A1 | 10/2004 | Patel et al. |
| 2004/0267273 A1 | 12/2004 | Whittaker et al. |
| 2004/0267274 A1 | 12/2004 | Patel et al. |
| 2005/0027301 A1 | 2/2005 | Stihl |
| 2005/0055029 A1 | 3/2005 | Marik et al. |
| 2005/0071013 A1 | 3/2005 | Zubok et al. |
| 2005/0137606 A1 | 6/2005 | Binder et al. |
| 2005/0159819 A1 | 7/2005 | McCormack et al. |
| 2005/0228399 A1 | 10/2005 | Kubo et al. |
| 2006/0025863 A1 | 2/2006 | Lamprich et al. |
| 2006/0121410 A1 | 6/2006 | Aravena |
| 2006/0122607 A1 | 6/2006 | Kolb |
| 2006/0129247 A1 | 6/2006 | Brown et al. |
| 2006/0200238 A1 | 9/2006 | Schmiel et al. |
| 2006/0212121 A1 | 9/2006 | Ferree |
| 2006/0241646 A1 | 10/2006 | Stihl |
| 2006/0271059 A1 | 11/2006 | Reay-Young et al. |
| 2006/0276800 A1 | 12/2006 | Lee et al. |
| 2007/0055286 A1 | 3/2007 | Ralph et al. |
| 2007/0083211 A1 | 4/2007 | Gonzalez et al. |
| 2007/0093848 A1 | 4/2007 | Harris et al. |
| 2007/0100347 A1 * | 5/2007 | Stad et al. ............... 606/90 |
| 2007/0100348 A1 | 5/2007 | Cauthen et al. |
| 2007/0123985 A1 | 5/2007 | Errico et al. |
| 2007/0233150 A1 | 10/2007 | Blain et al. |
| 2007/0276400 A1 | 11/2007 | Moore et al. |
| 2007/0276498 A1 | 11/2007 | Aebi et al. |
| 2008/0009881 A1 | 1/2008 | Blatt et al. |
| 2008/0015699 A1 | 1/2008 | Voydeville |
| 2010/0125277 A1 * | 5/2010 | Dace et al. ............... 606/96 |

FOREIGN PATENT DOCUMENTS

| | | |
|---|---|---|
| WO | WO-2004041131 | 5/2004 |
| WO | WO-2006078701 | 7/2006 |

* cited by examiner ated with the superior vertebral body and another one of the openings is in alignment with the inferior vertebral body. Referring to FIG. 46 of the '808 application, with pin drill guide 194 in place, holes are drilled in the superior and inferior vertebral bodies using a drill bit and the pins are placed in the holes.

ADJUSTABLE PIN DRILL GUIDE AND METHODS THEREFOR

BACKGROUND OF THE INVENTION

The present invention is directed to an adjustable pin drill guide and methods for inserting pins into adjacent vertebral bodies for use during a spinal surgical procedure.

U.S. patent application Ser. No. 11/439,808 ("the '808 application"), which was filed on May 20, 2006 and which is hereby incorporated by reference herein, describes the placement of pins in adjacent vertebral bodies using a pin drill guide. As described in the '808 application, after removal of disc tissue between adjacent vertebral bodies and placement of midline score marks and tack openings in adjacent vertebral bodies, pins are attached to the anterior faces of the bodies, for use in guiding other instruments during the surgical procedure disclosed therein. The pins are inserted using a pin drill guide, as shown as element 194 in at least FIGS. 11A-11D of the '808 application, that is partially inserted into the dissected disc space.

Specifically, referring to FIG. 45 of the '808 application, a head or extension 214 at a distal end 196 of pin drill guide 194 is inserted into the disc space between the vertebral bodies until vertebral body stops 222 and 224 abut against the anterior faces of the superior and inferior vertebral bodies. The pin drill guide is preferably aligned with the midline of the vertebral bodies (e.g., as marked by the score line markings) prior to this insertion. At this stage, one of the openings 210 or 212 in a main body 204 of pin drill guide 194 is preferably in alignment with the superior vertebral body and another one of the openings is in alignment with the inferior vertebral body. Referring to FIG. 46 of the '808 application, with pin drill guide 194 in place, holes are drilled in the superior and inferior vertebral bodies using a drill bit and the pins are placed in the holes.

Using pin drill guide 194 as described above does not allow for size variations of dissected disc space. That is, the pin drill guide is only applicable for a specific size of dissected disc space. Thus, multiple sizes of pin drill guides 194 may be needed for various patients. Accordingly, a need exists to overcome, inter alia, the above stated limitations.

BRIEF SUMMARY OF THE INVENTION

Disclosed herein is an adjustable pin drill guide and procedures in accordance with certain embodiments of the present invention. It is contemplated, however, that the instruments and procedures may be slightly modified, and/or used in whole or in part and with or without other instruments or procedures, and still fall within the scope of the present invention. Although the present invention may discuss a series of steps in a procedure, the steps can be accomplished in a different order, or be used individually, or in sub groupings of any order, or in conjunction with other methods, without deviating from the scope of the invention.

A first aspect of the present invention is a method of preparing an intervertebral body space to receive an implant. In accordance with certain embodiments of this first aspect, the method includes the steps of providing an adjustable pin drill guide including a first member having a first opening and a first extension and a second member having a second opening and a second extension; removing at least some of the tissue between a first vertebral body and a second vertebral body; inserting the first extension and the second extension of the adjustable pin drill guide in a first position between the first and second vertebral bodies; moving the first extension and the second extension from a first position to a second position, the first and second extensions being in parallel planes with one another in at least the first and second positions; drilling a first hole into the first vertebral body; drilling a second hole into the second vertebral body; placing a first pin in the first hole; and placing a second pin in the second hole.

A second aspect of the present invention is another method of preparing a vertebral body space to receive an implant. In accordance with certain embodiments of this second aspect, the method includes the steps of providing an adjustable pin drill guide including a first member having a first extension and a first opening and a second member having a second extension and a second opening wherein the first extension and second extension are provided in a first position; producing a gap between a first vertebral body and a second vertebral body by removing at least some of the tissue between the first vertebral body and the second vertebral body; inserting into the gap the first and second extensions in the first position; displacing the first extension and the second extension into a second position, the first and second extensions being in parallel planes in the second position; drilling through the first opening into the first vertebral body to create a first hole; drilling through the second opening into the second vertebral body to create a second hole; placing a first pin in the first hole; and placing a second pin in the second hole.

A third aspect of the present invention is an adjustable pin drill guide for preparing a vertebral body space to receive an implant. In accordance with certain embodiments of the present invention, the guide includes a first member and a second member in a first position, the first member having a first opening and a first extension extending from the distal end of the first member and the second member having a second opening and a second extension extending from the distal end of the second member. The first member and the second member are capable of moving to a second position, the first and second members being in parallel planes in the first and second positions and the first opening and second opening are designed for receiving a drill for creating holes in adjacent vertebral bodies while in the second position.

It should be noted that features and methods and functionalities of the present invention, including but not limited to features and methods and functionalities for engaging one tool (or parts thereof) with one or more other tools (or parts thereof) or with the implants (or parts thereof), and vice-versa; for addressing, avoiding, manipulating, or engaging the patient's anatomy; for aligning one or more tools with anatomic or non-anatomic reference points; and for aligning the tools and implants with one another and/or a treatment space; are not and should not be limited to those embodied in and achieved by the structures and methods of the specific embodiments described and shown, but rather the structures and methods of the specific embodiments described and shown are merely examples of structures and methods that can achieve certain features and methods and functionalities of the present invention.

These and other embodiments of the present invention will be described in more detail below.

DETAILED DESCRIPTION

Figure 1:
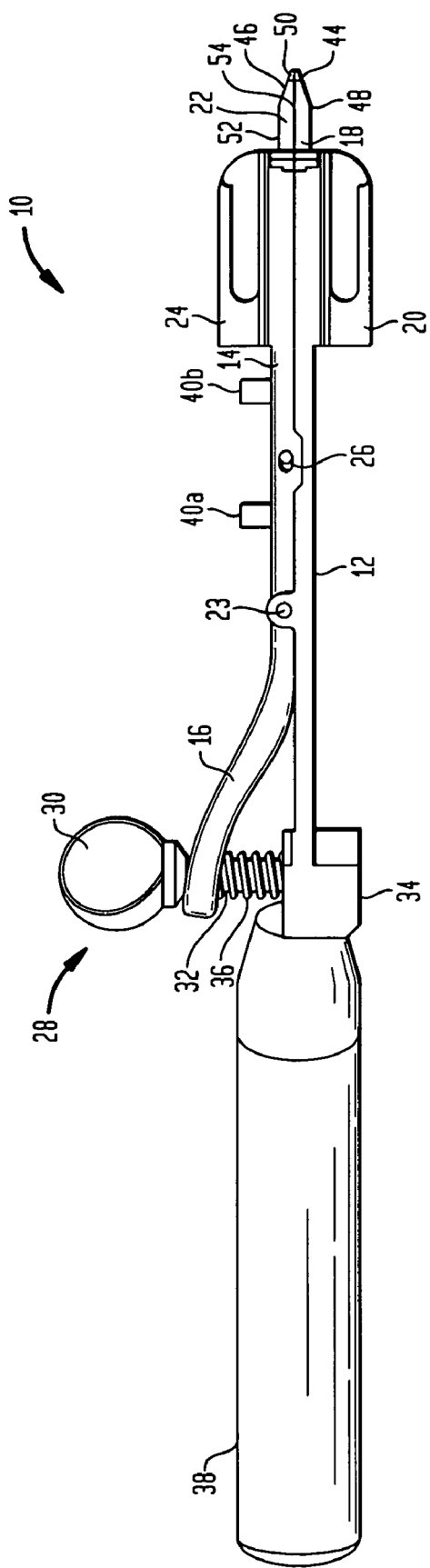
FIG. 1 is a side perspective view of an adjustable pin drill guide in accordance with one embodiment of the present invention, with a distal portion of the guide in a first position.

Referring to FIG. 1, in accordance with at least one embodiment of the present invention, an adjustable pin drill guide 10 is shown as including a first member 12, a second member 14, and a third member 16. First member 12 includes a first extension 18 and a first opening 20 at its distal end, and a channel 21 (best shown in FIGS. 3-5) near its proximal end. Similarly, second member includes a second extension 22 and a second opening 24 at its distal end, and an open channel 25 (best shown in FIGS. 3-5) at its proximal end. Third member 16 is shown as being movably connected to first member 12 and second member 14. In particular, third member 16 is attached to first member 12 by a pin connection 23 and to second member 14 by a pin connection 26. At least a portion of third member 16 is adapted for insertion into channel 21, while another portion is adapted for insertion into channel 25. Although described as pin connections, any pivotable coupling between third member 16 and first member 12 and between third member 16 and second member 14 can be used.

The operation and use of adjustable pin drill guide 10, including additional details relating to the interrelationship among the first, second, and third members, are discussed below.

Adjustable pin drill guide 10 also includes a displacer 28 (shown as a thumb screw in the drawings), which includes a user interface section 30 and threaded section 32. Threaded section 32 is sized and configured for cooperation with a displacer receiver 34 connected with first member 12. Essentially, receiver 34 is a body having a threaded hole that accepts threaded section 32 therein. However, other configurations for this cooperation are contemplated, for instance, a ratchet mechanism or the like. A spring or other resilient member 36 is provided between first member 12 and third member 16. In the particular embodiment shown in the drawings, spring 36 is provided along threaded section 32 and in contact with receiver 34 and third member 16. Other configurations are contemplated, for instance, a resilient member that is between first member 12 and third member 16, and not along threaded section 32.

Moreover, drill guide 10 includes handle 38 which is preferably adapted for gripping by a surgeon. While shown as connected with receiver 34, it is to be understood that other embodiments may have handle 38 attached to different element(s) or configured differently. In some embodiments, handle 38 is designed for improved gripping by the surgeon (e.g., it may include rubber, surface roughening, or the like). In addition, the handle may also include different ergonomic designs and may be provided in different sizes. Other embodiments of the present invention include handles 38 that are detachable from the remainder of guide 10, so that different handle designs may be provided and selected from.

Figure 2:
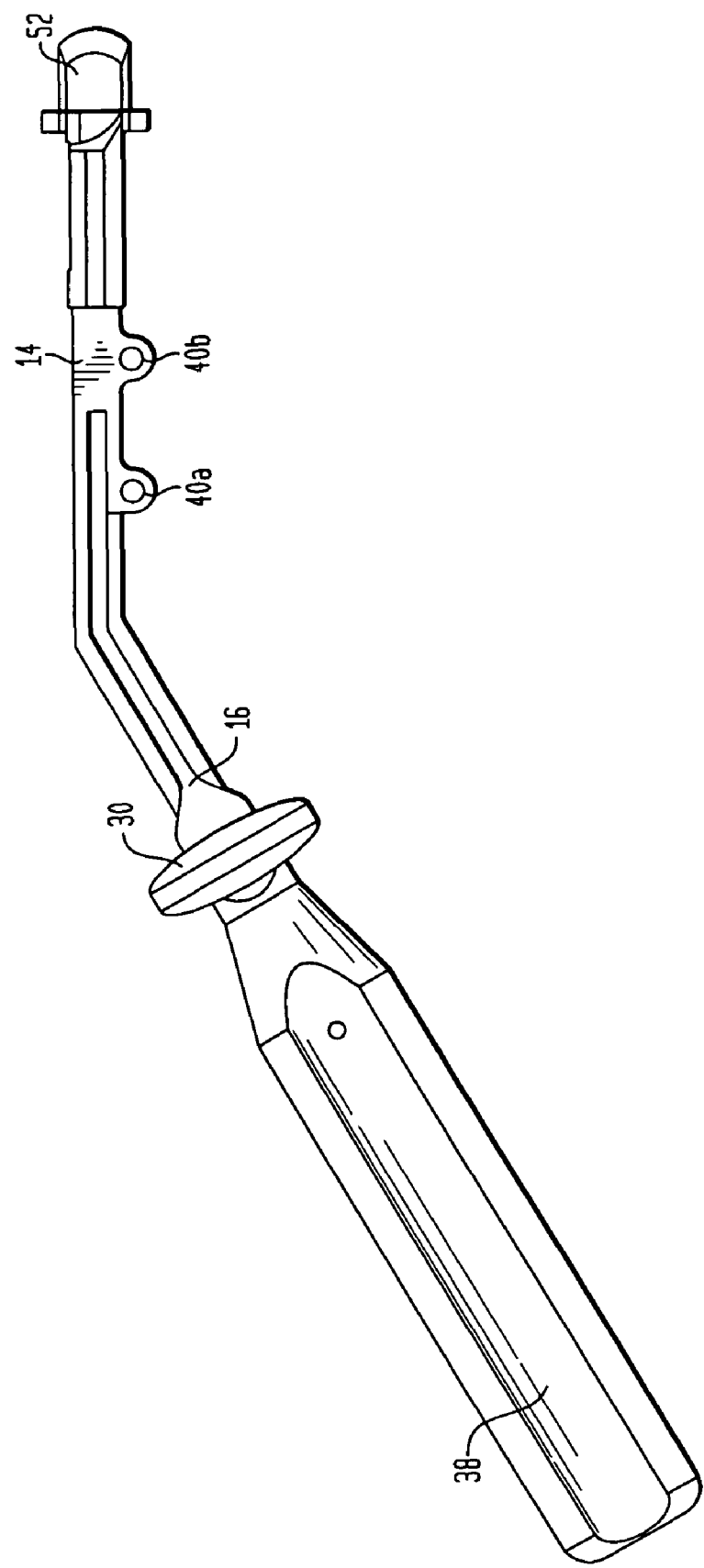
FIG. 2 is a top perspective view of the adjustable pin drill guide of FIG. 1.

As is best shown in FIG. 2, second member 14 is substantially straight along its length, while portions of first member 12 and third member 16 are curved. Specifically, a portion of first member 12 is curved in a left to right direction in the view of FIG. 2, while portions third member 16 are curved in two directions, upwardly in the view of FIG. 1 and from left to right in the view of FIG. 2. Third member 16 also includes a portion that is parallel with first member 12, and it is in this parallel region that those members are moveably coupled to each other. It is to be understood that the particular configuration shown in the drawings can differ significantly. For example, as is best shown in FIG. 2, guide 10 is configured in a manner which allows for handle 38 to be displaced to one side. This preferably aids in the use of guide 10 by allowing the surgeon a clearer line of sight into the area of the spine in which the surgical procedure is being conducted. In the design shown in FIG. 2, handle 38 is displaced to the right side of that surgical area. However, it is contemplated that the elements of guide 10 could be designed so as to displace the handle to the left side of the surgical area. This choice may be beneficial depending upon whether the surgeon is left or right handed. Furthermore, displacing the handle above or below the surgical area is also contemplated.

In operation, third member 16 moves in the direction toward and away from first member 12 upon threading of displacer 28 into displacer receiver 34. This threading overcomes the force spring 36 provides upon third member 16, which preferably acts to hold the third member towards interface section 30 of displacer 28, as well as to keep guide 10 in the position shown in FIG. 1. Upon tightening of displacer 28 and movement of a distal portion of third member 16 towards a distal portion of first member 12 (best shown in the progression of FIGS. 3-5), more and more of a portion of the third member becomes situated in channel 21. Because of the pivotal connections between third member 16 and both first and second members 12 and 14, this movement also causes second member 14 to move away from first member 12.

To assure that the first and second members remain in parallel planes with respect to each other, first member 12 is provided with pins 40*a* and 40*b* that are adapted to cooperate with apertures 42*a* and 42*b* formed in a portion of second member 14. That coupled with the pivotal nature of the connection between second member 14 and third member 16 allows for the desired parallel displacement. While pins 40*a* and 40*b* and apertures 42*a* and 42*b* are shown situated to one side of guide 10 (to remove them from the surgeon's line of sight), it is noted that other configurations are contemplated, including, but not limited to, the other side of the guide. Likewise, while two circular pins 40*a* and 40*b* are shown cooperating with two circular apertures 42*a* and 42*b*, other configurations contemplated. For instance, one pin and one aperture may be provided, and other shapes such as square, rectangular, oval, star shaped, or the like can be employed. Additionally, in other embodiments, first member 12 could include the apertures and second member could include the pins.

Figure 3:
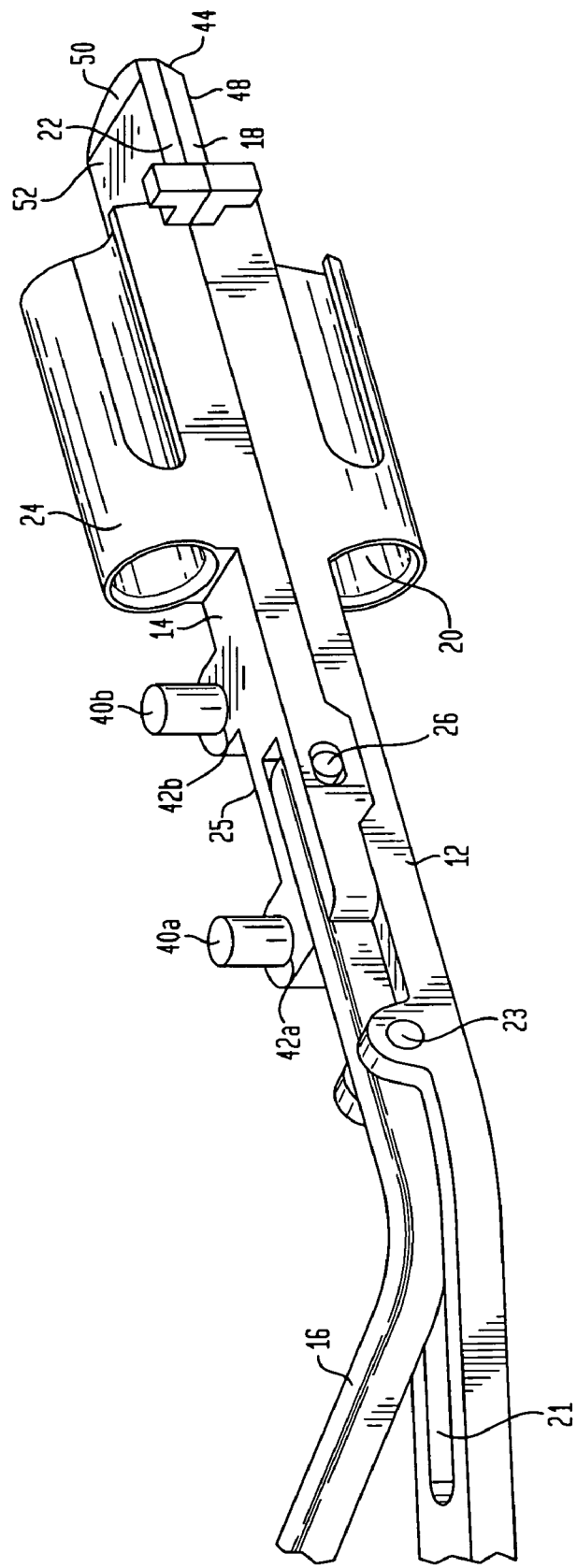
FIG. 3 is a right-side perspective view of the adjustable pin drill guide of FIG. 1.
Figure 4:
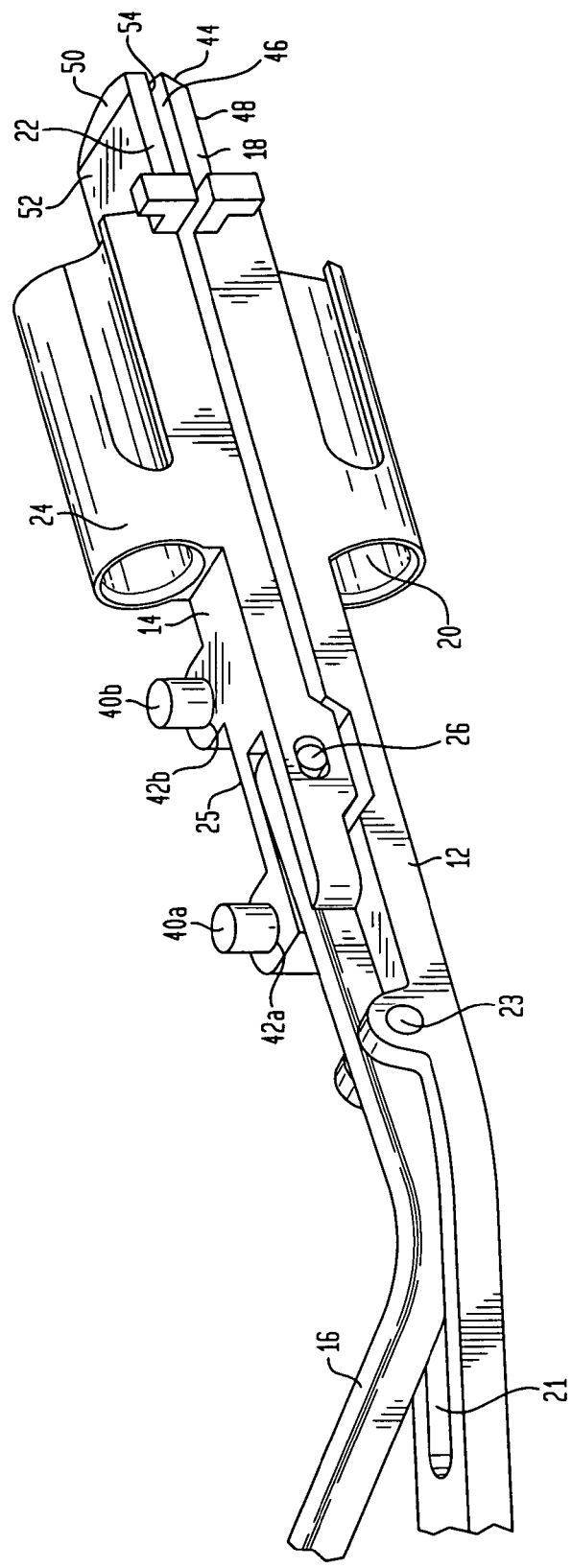
FIG. 4 is a right-side perspective view of the adjustable pin drill guide of FIG. 1, with the distal portion in an intermediate position.
Figure 5:
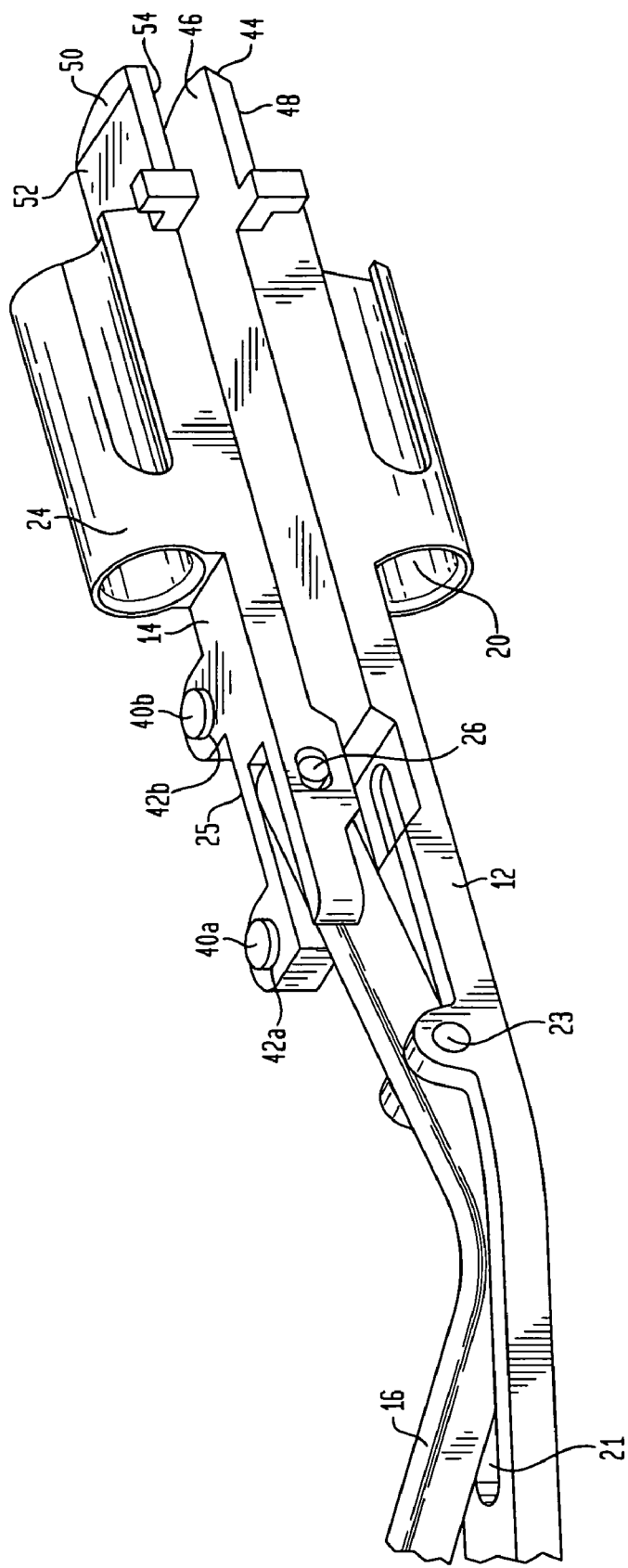
FIG. 5 is a right-side perspective view of the adjustable pin drill guide of FIG. 1, with the distal portion in a second position.

The above-discussed movement between first member 12 and second member 14 necessary moves first extension 18 and second extension 22 from their first and touching position shown in FIG. 3, through the intermediate position shown in FIG. 4, and ultimately to their second and spread position shown in FIG. 5. Throughout this movement, first member 12 (and first extension 18) and second member 14 (and second extension 22) remain parallel to each other. This is due to the above-discussed cooperation among the elements of guide 10. However, it is to be understood that other configurations may be employed that allow for non-parallel movement. For instance, guide 10 may be designed to allow for non-parallel positions in intermediate positions (with the first and second positions being in parallel planes) or for non-parallel first and second positions.

Guide 10 may be utilized during a surgical procedure, such as the one disclosed in the aforementioned '808 application. Specifically, guide 10 is useful in drilling pin holes in adjacent vertebral bodies in a similar fashion as is shown in FIGS. 45-49 of the '808 application. However, in some embodiments, guide 10 may be utilized in also performing the steps shown in FIGS. 50-53 of the '808 patent (i.e., placement of the pins).

Figure 6:
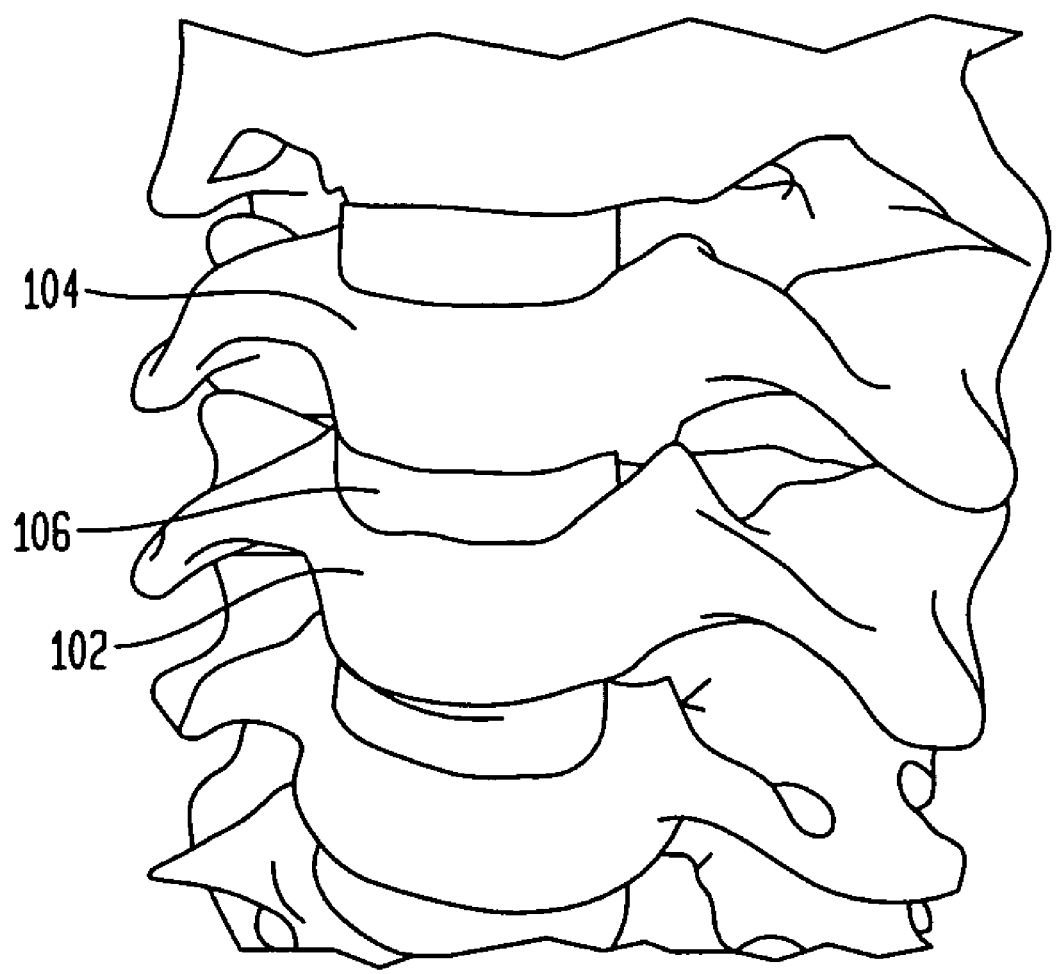
FIG. 6 is a perspective view of a portion of a human vertebral column.
Figure 7:
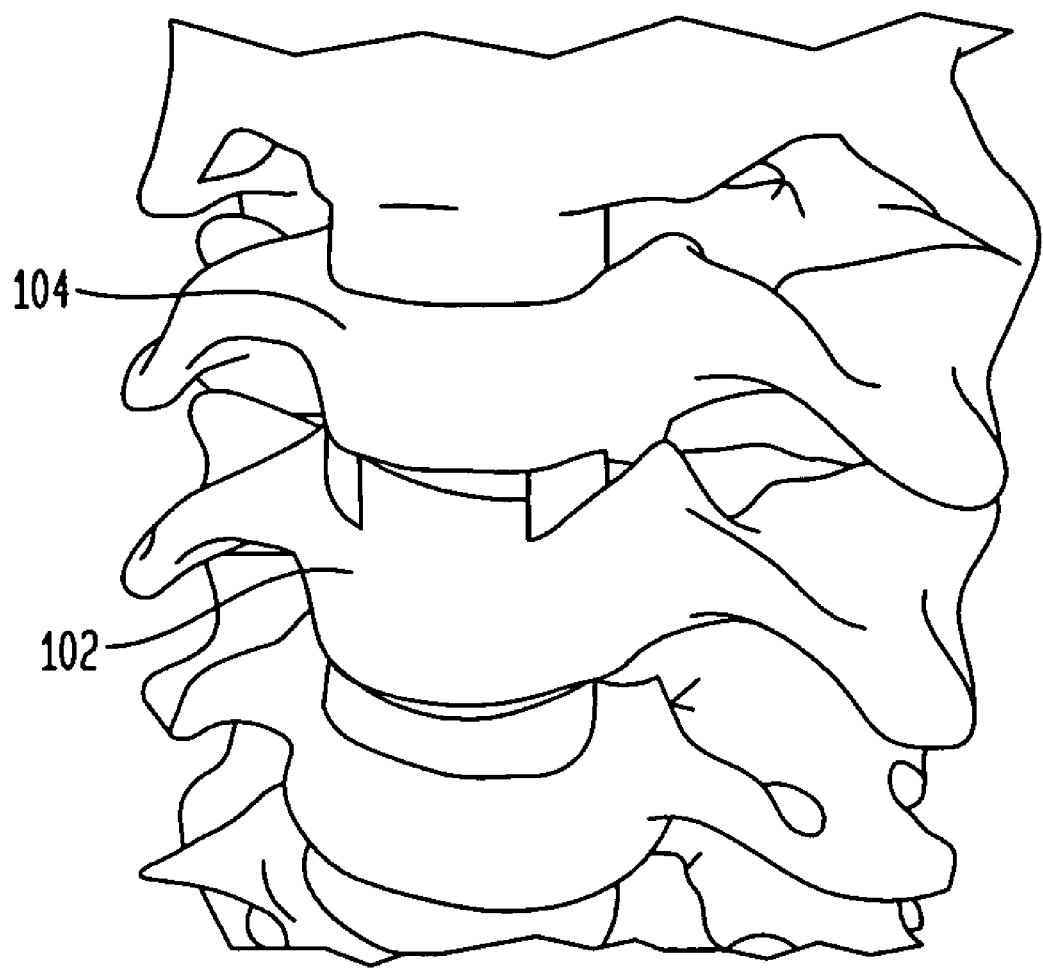
FIG. 7 is a perspective view of the portion of the vertebral column shown in FIG. 6, with a portion of a spinal disc removed between a first vertebral body and a second vertebral body.

For example, FIG. 6 of the present application illustrates a typical surgical site in which the present invention is utilized, including a first vertebral body 102, a second vertebral body 104, and an intervertebral disc 106. In a procedure (like the one disclosed in the '808 application), the surgeon first resects a portion of disc 106, which is often degenerated or in need of replacement for another reason. The surgical site subsequent to this resection step is shown in FIG. 7. In order to perform a lot of the surgical steps discussed in the '808 application, pins need to be inserted into vertebral bodies 102 and 104. Thus, subsequent to a marking step (shown in FIGS. 40-42 of the '808 application), first and second extensions 18 and 22 of guide 10 are inserted between the vertebral bodies.

In order to aid in this insertion, first extension 18 may include a tapered nose 44 in addition to a top surface 46 and a bottom surface 48. Likewise, second extension 22 may include a tapered nose 50 in addition to a top surface 52 and a bottom surface 54. Thus, when first extension 18 and second extension 22 are in the aforementioned first position (i.e., in parallel planes and touching), they act as one extension with a tapered nose, a top surface 52, and bottom surface 48. This construction preferably aids in the insertion of guide 10 into the space between vertebral bodies 102 and 104. Further still, first extension 18 and second extension 22 are shown as having substantially planar surfaces 46, 48, 52, and 54. However, it is to be understood that they include shapes more akin to the surfaces of the endplates of vertebral bodies 102 and 104. For instance, top surface 52 and bottom surface 48 may be concave or convex, in whole or in part, in order to better cooperate with the endplates of the vertebral bodies they are placed between. In the embodiment shown in the FIGS, first extension 18 and second extension 22 are each approximately 1.5 millimeters thick. This facilitates their easy insertion when in the first position.

Figure 8:
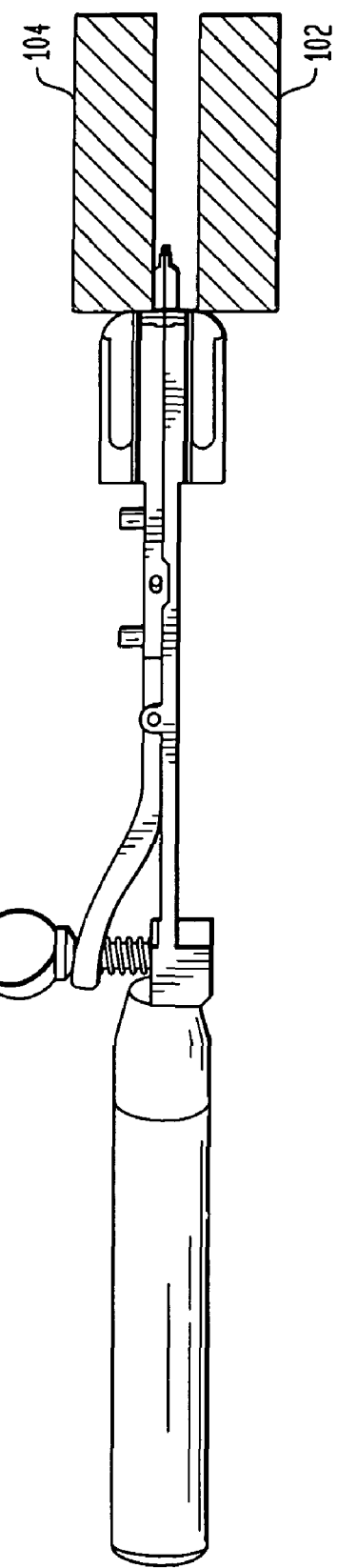
FIG. 8 is a cross sectional view of two adjacent vertebral bodies having the adjustable pin drill guide of FIG. 1 inserted therebetween.
Figure 9:
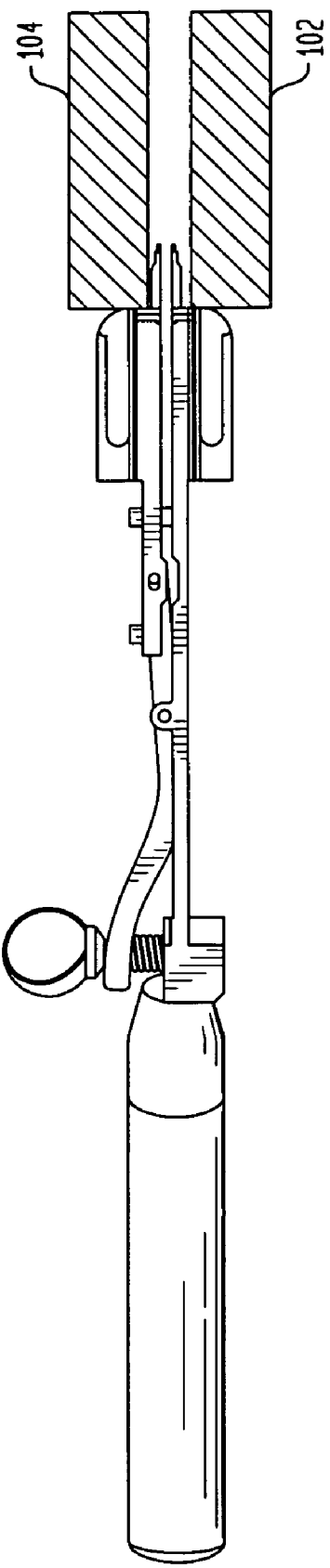
FIG. 9 is a cross sectional view of the two adjacent vertebral bodies of FIG. 8 having the adjustable pin drill guide of FIG. 4 inserted therebetween.
Figure 10:
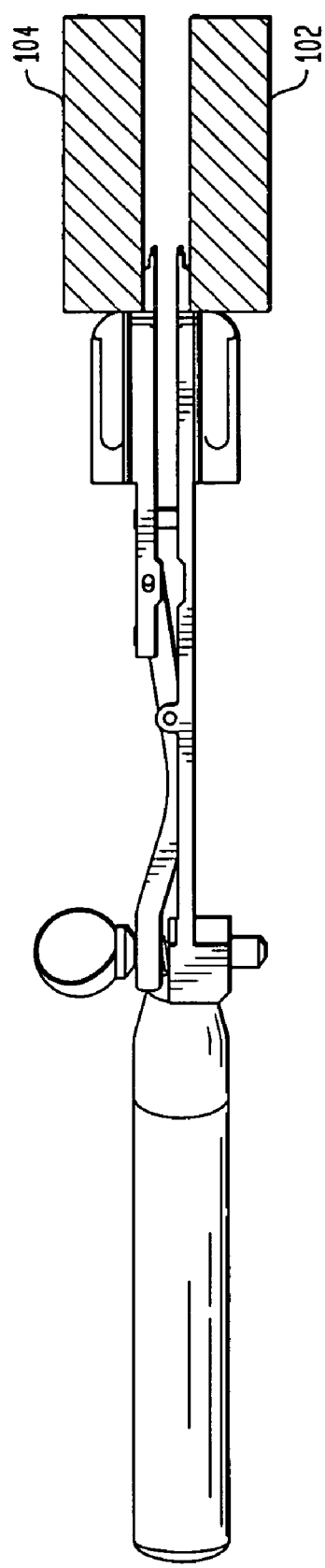
FIG. 10 is a cross sectional view of the two adjacent vertebral bodies of FIG. 8 having the adjustable pin drill guide of FIG. 5 inserted therebetween.

FIG. 8 illustrates guide 10 initially inserted between vertebral bodies 102 and 104. At this point, displacer 28 is operated to move first extension 18 towards vertebral body 102 and second extension 22 towards vertebral body 104. This movement between the aforementioned first and second positions (which was illustrated earlier in FIGS. 3-5) is shown in FIGS. 8-10 occurring between bodies 102 and 104. Ultimately, displacer 28 is operated until top surface 52 comes in contact with vertebral body 104 and bottom surface 48 comes in contact with vertebral body 102 (FIG. 10). In a preferred embodiment, no distraction of the vertebral bodies is caused by the expansion of guide 10, but rather, the expansion allows for the proper sizing of the space between the bodies. However in other embodiments, or if desired, guide 10 may be utilized to distract the vertebral bodies away from each other. The amount of distraction (or even the ability to) will dictated by the size of the various components of guide 10.

Figure 11:
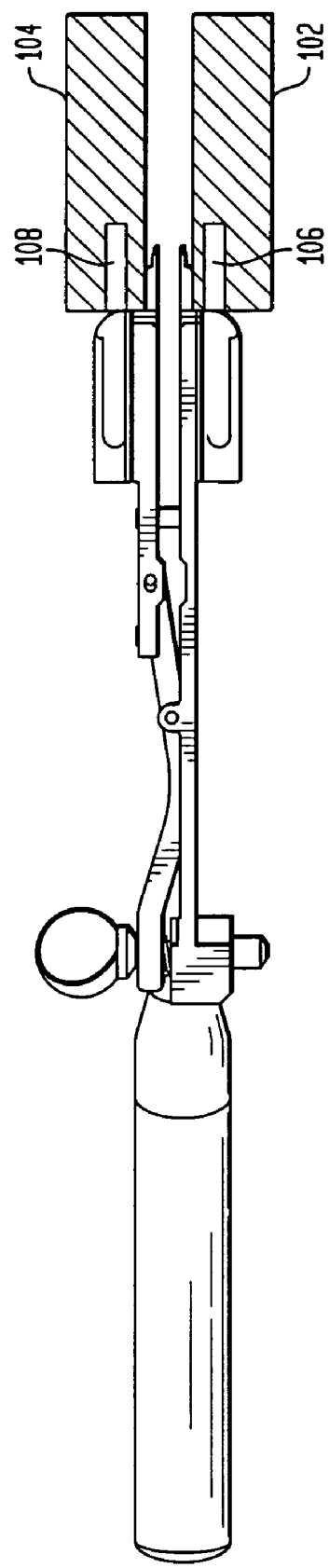
FIG. 11 is another cross sectional view similar to that of FIG. 10, subsequent to the drilling of holes in the vertebral bodies.
Figure 12:
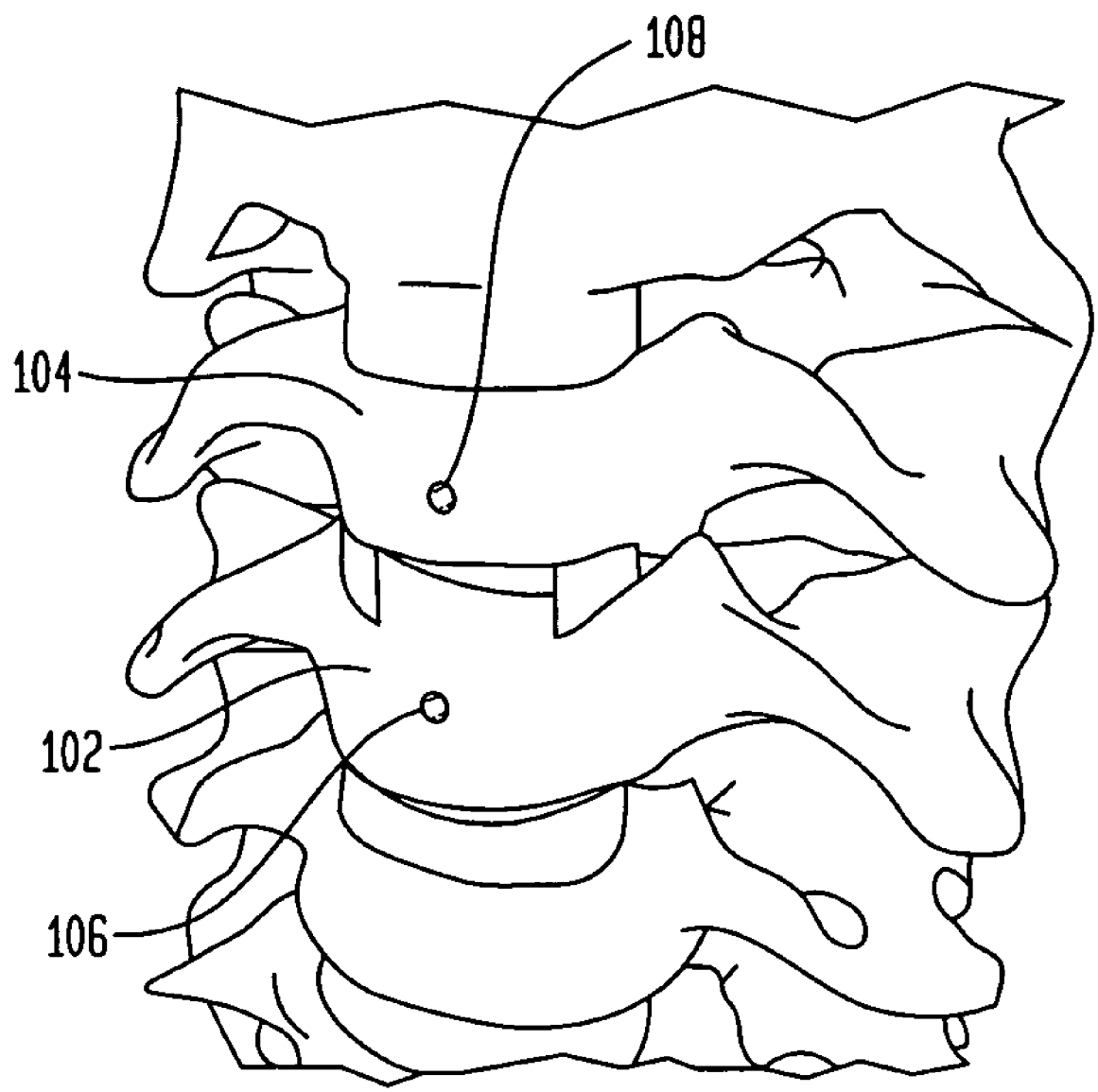
FIG. 12 is a perspective view similar to that of FIG. 7, subsequent to the drilling of holes in the vertebral bodies.
Figure 13:
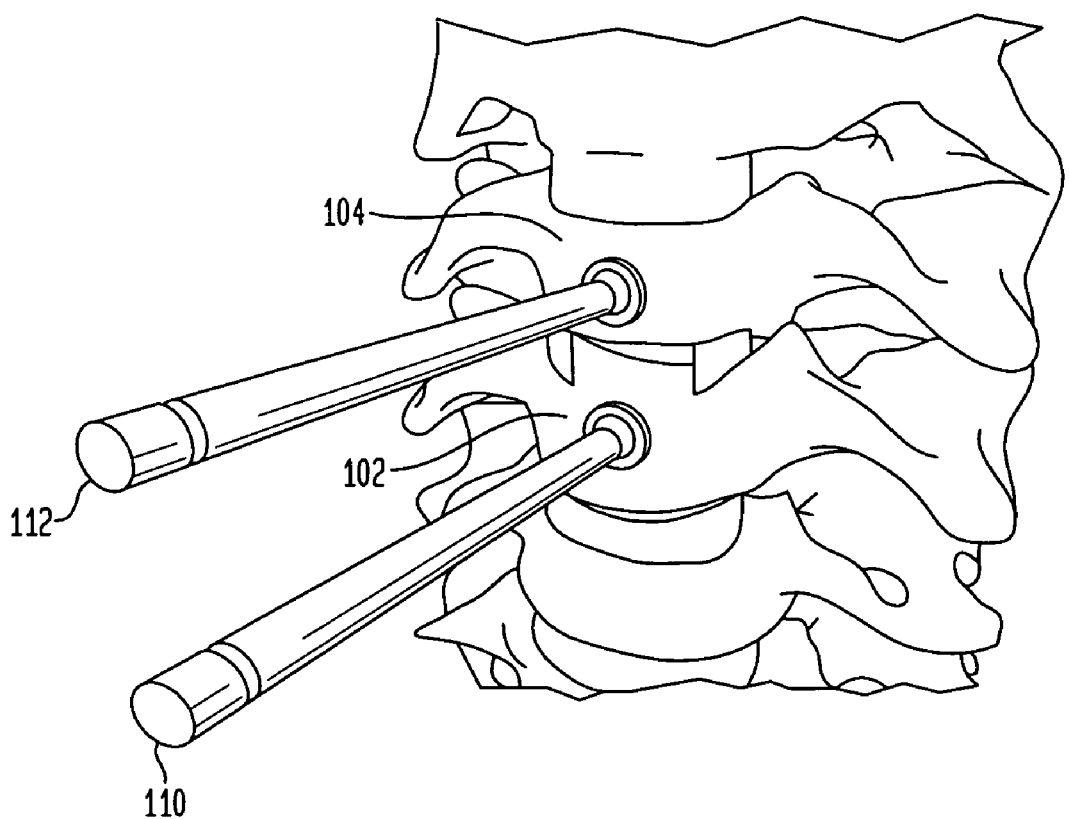
FIG. 13 is a perspective view similar to that of FIG. 12, with pins located in the holes drilled in the vertebral bodies.
Figure 14:
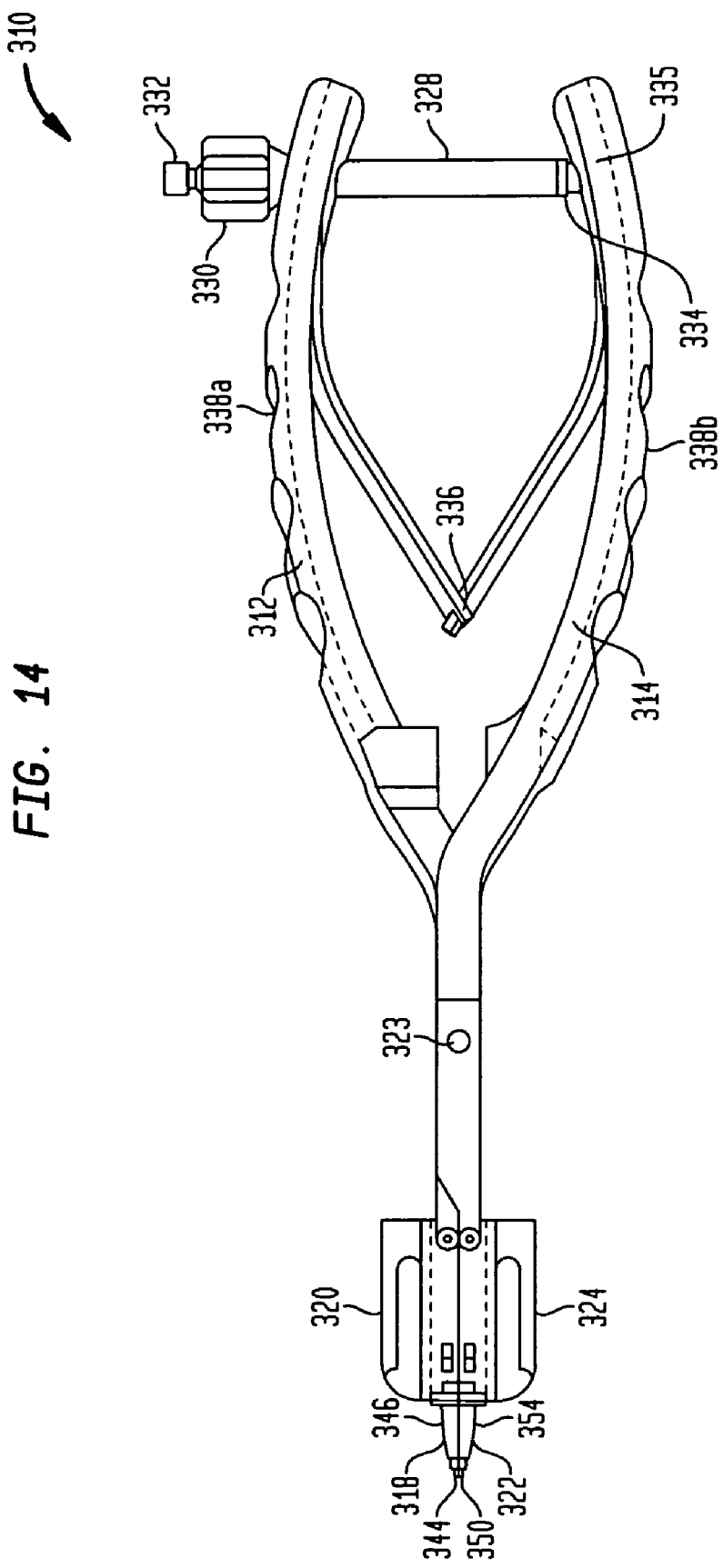
FIG. 14 is a side perspective view an adjustable pin drill guide in accordance with a second embodiment of the present invention, with a distal portion of the guide in a first position.

Once guide 10 is in the second position between bodies 102 and 104 (shown in FIG. 10), first opening 20 and second opening 24 are utilized to drill holes in the bodies to receive pins. The result of this drilling step is best illustrated in FIGS. 11 and 12. The configuration of guide 10 is such that after its expansion to the second position, openings 20 and 24 are aligned with the vertebral bodies to guide a drill to properly situate holes 106 and 108. First opening 20 and second opening 24 are sized so as to receive a drill bit, portion of a drill, or the like, similar to that disclosed in the '808 application (e.g., a stepped drill bit). Openings 20 and 24 may also be sized to accept pins therethrough and guide them into holes 56 and 58. In other words, act in a similar fashion as does reference pin guide 236 of the '808 application. In this regard, reference is made to both the placement of pins as described in the '808 patent, and FIG. 13 of the present invention (which shows pins 110 and 112 in first vertebral body 102 and second vertebral body 104, respectively). It is to be understood that the placement of pins through guide 10 may or may not involve the use of a pin sleeve or the like, as is described as element 290 in the '808 application.

In accordance with the present invention, it is noted guide 10 can be utilized to aid in the placement of pins in vertebral bodies of varying sizes, as well as in vertebral bodies being situated different distances from each other. For instance, as is discussed above, in the first position first extension 18 and second extension 22 may have a combined thickness of approximately 3 millimeters. As guide 10 is expanded, first extension 18 and second extension 22 move away from each other until they reach the second position, which may result in a total distance between top surface 52 and bottom surface 48 (i.e., the thickness) of approximately 7 millimeters. Of course, there are various intermediate positions in which this distance may be any one of the values between 3 and 7 millimeters. Depending upon the size and configuration of guide 10, an infinite amount of thicknesses may be provided by the guide.

Figure 15:
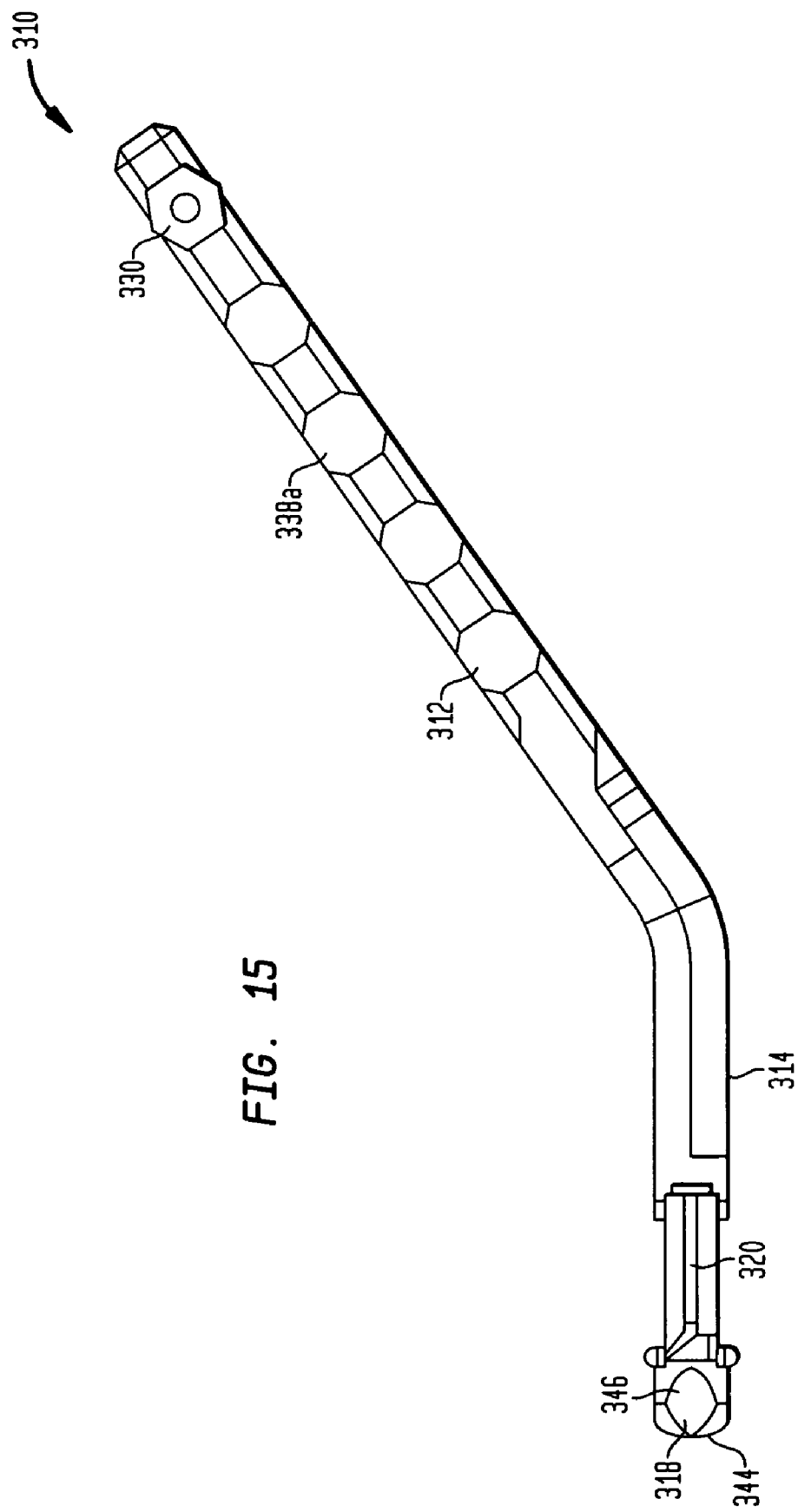
FIG. 15 is a top perspective view of the adjustable pin drill guide of FIG. 14.

Referring to FIGS. 14-21, a second embodiment adjustable pin drill guide 310 is shown. Because of the similarities of many of the elements of guide 310 and that of above-discussed guide 10, similar elements are labeled with like reference numerals within the 300-series of numbers. For instance, guide 310 includes a first member 312 and second member 314. First member 312 includes a first extension 318 and a first opening 320 at its distal end, and second member includes a second extension 322 and a second opening 324 at its distal end. First and second members 312 and 314 are connected to each other via a pin connection 323, thereby allowing for pivotal movement of the members with respect to each other. As is best shown in FIG. 15, the first and second members cooperate with each other in a somewhat different fashion as do the first, second, and third members of guide 10. First and second members 312 and 314 of guide 310 are designed to include portions which oppose one another and portions which lie side by side with one another. These side by side portions (i.e., the distal portions of members 312 and 314) are connected by pin connection 323. Of course, as is the case with guide 10, any similar connection can be utilized and connected to the members.

Figure 16:
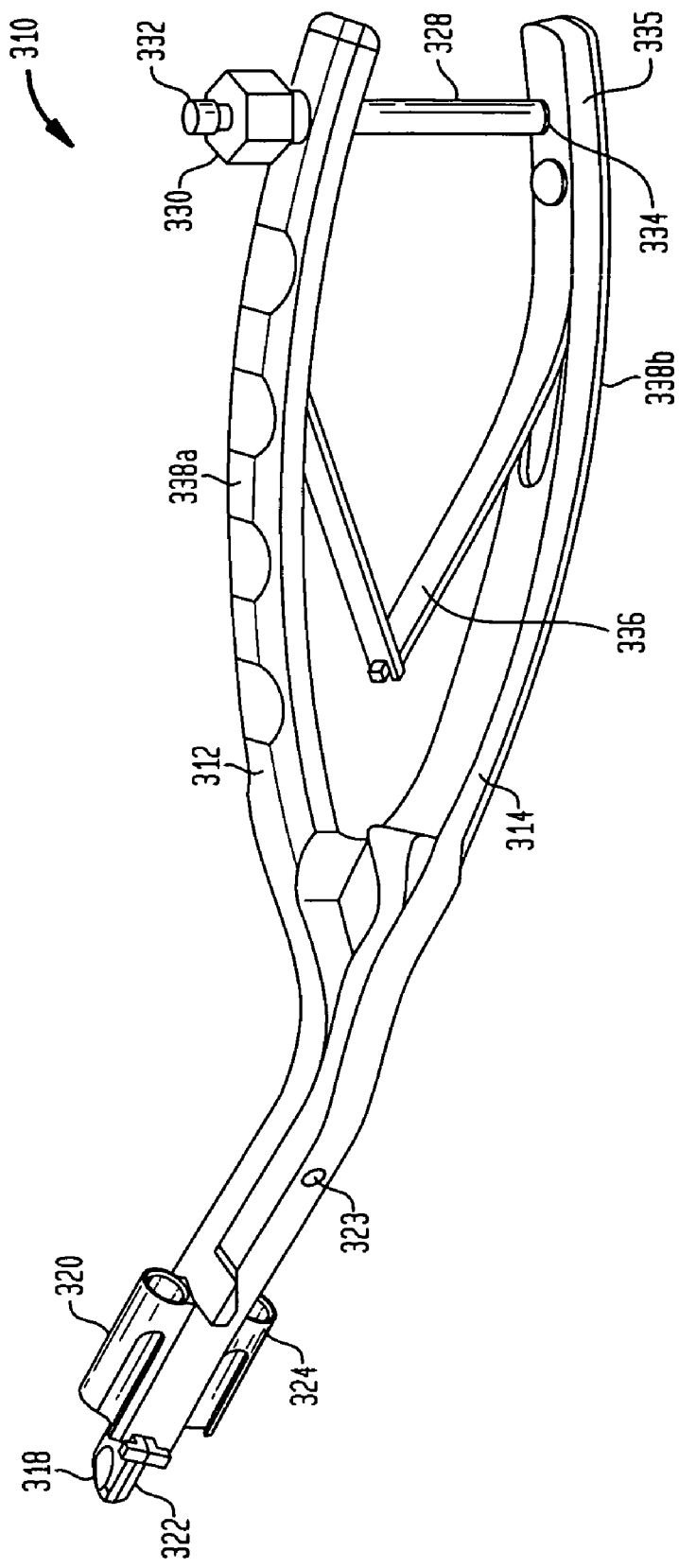
FIG. 16 is left-side perspective view of the adjustable pin drill guide of FIG. 14.
Figure 17:
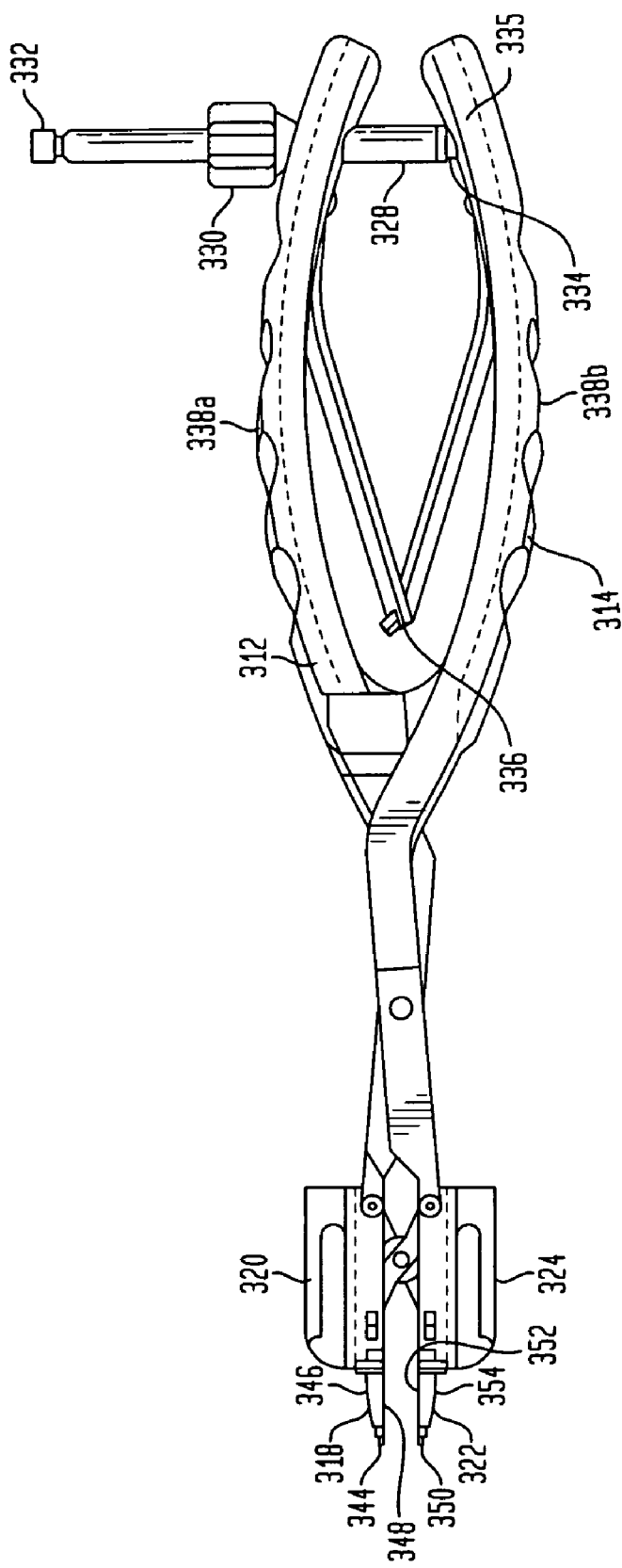
FIG. 17 is a side perspective view of the adjustable pin drill guide of FIG. 14, with the distal portion in a second position.
Figure 18:
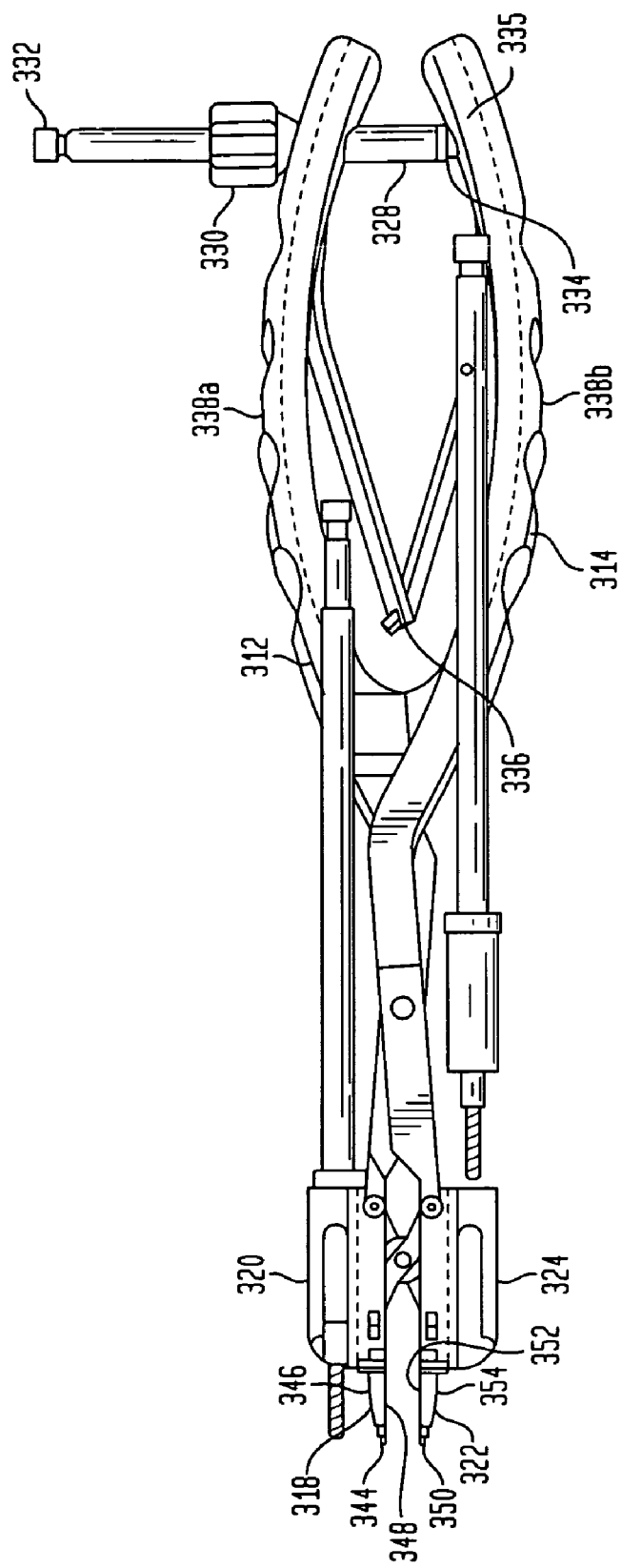
FIG. 18 is a side perspective view similar to that of FIG. 17, with drill elements associated with the adjustable pin drill guide.

Also like guide 10, adjustable pin drill guide 310 includes a displacer 328 including a first threaded end 332 and a second end 334 attached via a pin 335 to second member 314. A user interface section or nut 330 is provided for cooperation with first threaded end 332. Thus, upon threading of nut 330 on threaded section 332, first member 312 is displaced towards second member 314. The cooperation between second end 334 and pin 335 allows for at least the partial rotation of displacer 328 with respect to second member 314. This ensures the proper application of forced to first and second members 312 and 314. Essentially, displacer remains in a vertical position while the first and second members move towards on another. This is best shown in FIGS. 16-18. Other configurations for displacer 328 are contemplated. For instance, first end 332 and user interface second 330 could be cooperating ratchet mechanisms or the like. A leaf spring or other resilient member 336 is provided between first member 312 and second member 314. Spring 336 acts to push the proximal portions of first and second members 312 and 314 away from one another absent a force being applied to overcome its force.

The aforementioned proximal portions of first and second members 312 and 314 make up a handle which is similar to handle 38 of above-discussed guide 10. Specifically, first member 312 includes handle portion 338a and second member 314 includes a handle portion 338b. Like in guide 10, the handle of guide 310 may include elements designed for improved gripping by the surgeon (e.g., it may include rubber, surface roughening, or the like). For instance, portions 338a and 338b are shown in the drawings to include surfaces designed to improve gripping of the device. In other embodiments, only one of the handle portions may include such a surface and/or the surfaces can be differently designed. In addition, the handle may also include differently sized handle portions 338a and 338b to therefore provide in different overall handle sizes. Any combination of the various handle portions is contemplated. As is best shown in FIG. 15, guide 310 provides a similar curved profile as in the above-discussed guide 10. Specifically, portions of first and second members 312 and 314 are curved in a right to left direction, thereby aiding in the use of guide 310 by allowing the surgeon a clearer line of sight into the area of the spine in which the surgical procedure is being conducted. Also similar to guide 10, guide 310 may include other configurations in which the handle or other elements of guide 310 are displaced in different directions. This includes in the opposite left to right direction, as well as above and below the surgical area.

In operation, movement of first member 312 towards second member 314 causes movement of first extension 318 and second extension 322 away from each other. The movement of the first and second members towards one another is preferably created by the threading of displacer 328 into displacer receiver 334, but may be created through the simple squeezing of handle portions 338a and 338b towards each other. Either of these operations would overcome the force spring 336 provides upon first and second members 312 and 314, with the former retaining the first and second members in this position. Because of the pivotal connections between first and second members 312 and 314, handle portions 338A and 338B move towards one another, while more distal portions of the first and second members move away from each other. This is best shown in FIG. 17.

Figure 19:
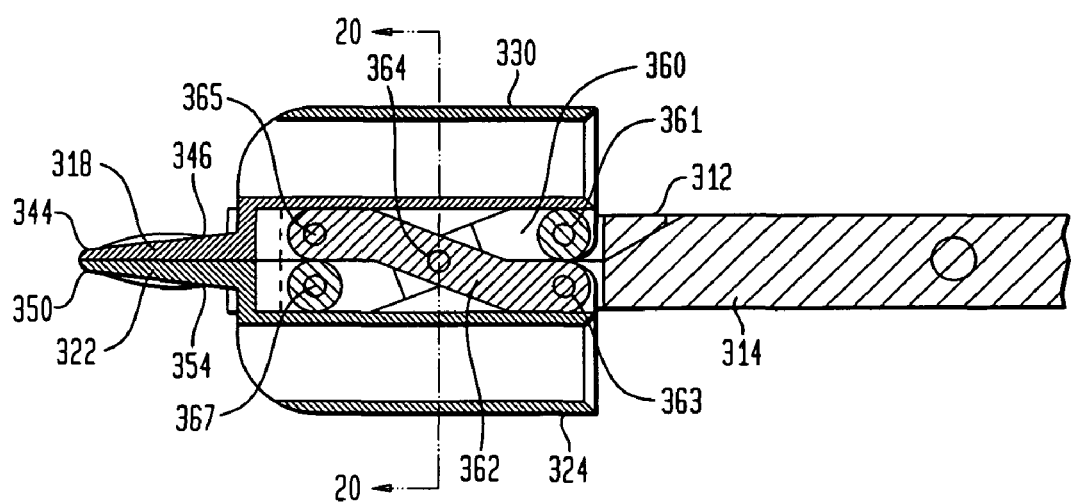
FIG. 19 is a side perspective view of the distal portion of the adjustable pin drill guide of FIG. 14.
Figure 20:
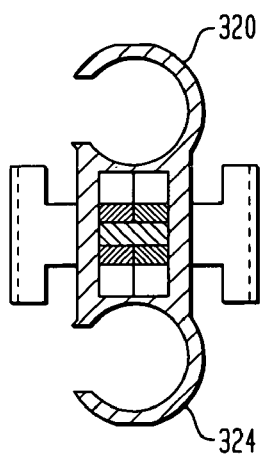
FIG. 20 is a view of the distal portion taken along line A-A of FIG. 19.
Figure 21:
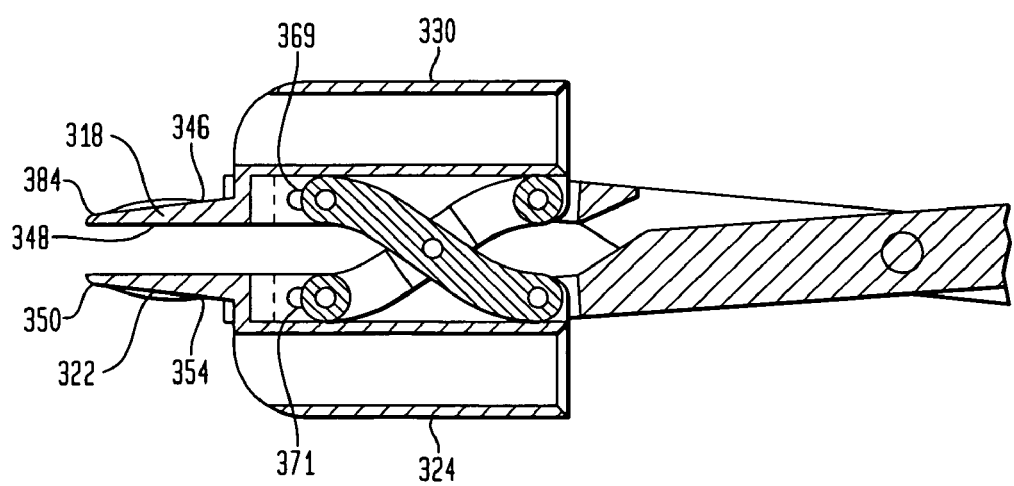
FIG. 21 is a side perspective view of the distal portion of the adjustable pin drill guide of FIG. 17.

To assure that first extension 318 and second extension 322 remain in parallel planes with respect to each other, guide 310 is provided with a detailed linkage assembly best shown in FIGS. 19 and 21. In particular, this linkage assembly includes a first bar 360 pivotably connected to a distal portion of first member 312 via a pin connection 361 and a proximal portion of second extension 322 via a pin connection 367. The assembly also includes a second bar 362 pivotably connected with to a distal portion of second member 314 via a pin connection 363 and a proximal portion of first extension 318 via a pin connection 365. Furthermore, first and second bars 360 and 362 are connected to one another via a pivot point 364. Pin connections 361 and 363 only allow for simple rotation of first bar 360 with respect to first member 312 and second bar 362 with respect to second member, respectively. On the other hand, first bar 360 is connected to second extension 322 via a pin connection 367 which is permitted to slide within a slot 371 formed on a proximal portion of second extension 322 and second bar 362 is attached to first extension 318 via a pin connection 365 which is also permitted to slide within a slot 369 formed on a proximal portion of first extension 318 (best shown in FIG. 21). These similar pin and slot connections allow for both rotational and sliding movements. As is best shown in FIGS. 19 and 21, upon movement of first and second handle portions 338A and 338B towards one another, these configurations causes the first and second extensions 318 and 322 to move away from each other in parallel planes. FIG. 20 shows a cross-section taken through pivot point 364.

The above-discussed movement between first member 312 and second member 314 necessarily moves first extension 318 and second extension 322 from their first and touching position shown in FIGS. 14, 15, 16, 19, and 20, to their second and spread position shown in FIGS. 17, 18, and 21. Throughout this movement, and because of the linkage assembly discussed above, at least first extension 318 and second extension 322 remain parallel to each other. However, it is understood that other configurations may be employed that allow for non-parallel movement. For instance, guide 310 may be designed to allow for non-parallel positions in intermediate positions (with or without the first and second positions being in parallel planes) or for non-parallel first and second positions. Guide 310 may be utilized in a similar fashion as is discussed above in connection with guide 10. However, it is noted that guides 10 or 310 may be utilized in different circumstances, depending upon various factors, including patient anatomy, etc.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing a vertebral body space to receive an implant, comprising:
    providing an adjustable pin drill guide including: a first member having a first opening and a first extension, and a second member having a second opening and a second extension;
    removing at least some of the tissue between a first vertebral body and a second vertebral body;
    inserting the first extension and the second extension of the adjustable pin drill guide in a first position between the first and second vertebral bodies;
    moving the first extension and the second extension from a first position to a second position, the first and second extensions being in parallel planes with one another in at least the first and second positions;
    drilling a first hole into the first vertebral body;
    drilling a second hole into the second vertebral body;
    placing a first pin in the first hole; and
    placing a second pin in the second hole,
    wherein in the second position the first and second extensions contact the first and second vertebral bodies.

2. The method as claimed in claim 1, wherein the placing steps are performed through the first and second openings of the drill guide.

3. The method as claimed in claim 2, wherein subsequent to placing the first pin in the first hole a sleeve is placed over the first pin.

4. The method as claimed in claim 1, wherein the first and second members are touching in the first position.

5. The method as claimed in claim 1, wherein the adjustable pin drill guide further includes a third member for displacing the second member.

6. The method as claimed in claim 1, wherein the first and second extensions are movable between a first position defining a thickness of about 3 millimeters and a second position defining a thickness of about 7 millimeters.

7. A method of preparing a vertebral body space to receive an implant, comprising:
    providing an adjustable pin drill guide including:
    a first member having a first extension and a first opening and a second member having a second extension and a second opening wherein the first extension and second extension are provided in a first position;
    producing a gap between a first vertebral body and a second vertebral body by removing at least some of the tissue between the first vertebral body and the second vertebral body;
    inserting into the gap the first and second extensions in the first position;
    displacing the first extension and the second extension into a second position, the first and second extensions being in parallel planes in the second position;
    drilling through the first opening into the first vertebral body to create a first hole;
    drilling through the second opening into the second vertebral body to create a second hole;
    placing a first pin in the first hole through the first opening;
    placing a second pin in the second hole through the second opening; and
    placing a sleeve over the first pin.

8. The method of claim 7, wherein in the second position the first extension contacts the first vertebral body and second extension contacts the second vertebral body.

9. The method of claim 7, wherein the first position has a thickness of about 3 millimeters and the second position has a thickness of about 7 millimeters.

* * * * *